United States Patent
Muthusamy

(10) Patent No.: US 10,450,255 B2
(45) Date of Patent: *Oct. 22, 2019

(54) PROCESS FOR THE PREPARATION OF GLYCOLS

(71) Applicant: SHELL OIL COMPANY, Houston, TX (US)

(72) Inventor: Duraisamy Muthusamy, Houston, TX (US)

(73) Assignee: SHELL OIL COMPANY, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/763,714

(22) PCT Filed: Sep. 27, 2016

(86) PCT No.: PCT/EP2016/073006
§ 371 (c)(1),
(2) Date: Mar. 27, 2018

(87) PCT Pub. No.: WO2017/055289
PCT Pub. Date: Apr. 6, 2017

(65) Prior Publication Data
US 2018/0282249 A1    Oct. 4, 2018

Related U.S. Application Data

(60) Provisional application No. 62/234,125, filed on Sep. 29, 2015.

(51) Int. Cl.
*C07C 29/60*  (2006.01)
*C07C 29/132* (2006.01)

(52) U.S. Cl.
CPC ............ *C07C 29/60* (2013.01); *C07C 29/132* (2013.01)

(58) Field of Classification Search
None
See application file for complete search history.

(56) References Cited

U.S. PATENT DOCUMENTS

| 6,291,725 B1 * | 9/2001 | Chopade | C07C 29/00 |
| | | | 568/861 |
| 2004/0030200 A1 * | 2/2004 | Zeller | C07C 29/16 |
| | | | 568/876 |

FOREIGN PATENT DOCUMENTS

WO   2015028398 A1   3/2015

OTHER PUBLICATIONS

International Search Report and Written Opinion received for PCT Patent Application No. PCT/EP2016/073006, dated Nov. 30, 2016, 8 pages.
Ji et al., "Direct Catalytic Conversion of Cellulose into Ethylene Glycol Using Nickel-Promoted Tungsten Carbide Catalysts", Angewandte Chemie Int. Ed., vol. 47, Issue No. 44, Oct. 20, 2008, pp. 8510-8513.

* cited by examiner

*Primary Examiner* — Clinton A Brooks
*Assistant Examiner* — Kofi Adzamli

(57) ABSTRACT

A process for the preparation of glycols from a saccharide-containing feedstock comprising the steps of: (a) preparing a reaction mixture in a reactor vessel comprising the saccharide-containing feedstock, a solvent, a catalyst component with retro-aldol catalytic capabilities and a first hydrogenation catalyst comprising an element selected from groups 8, 9 and 10 of the periodic table; (b) supplying hydrogen gas to the reaction mixture in the reactor vessel; (c) monitoring the activity of the first hydrogenation catalyst; (d) preparing a second hydrogenation catalyst by contacting in a reactor a catalyst precursor comprising one or more elements selected from chromium and groups 8, 9, 10 and 11 of the periodic table with hydrazine to convert the catalyst precursor into the second hydrogenation catalyst; (e) when the hydrogenation activity declines, supplying the second hydrogenation catalyst to the reactor vessel to supplement the declined hydrogenation activity in the reactor vessel.

10 Claims, 2 Drawing Sheets

PROCESS FOR THE PREPARATION OF GLYCOLS

PRIORITY CLAIM

The present application is the National Stage (§ 371) of International Application No. PCT/EP2016/073006, filed 27 Sep. 2016, which claims priority from U.S. Provisional Application No. 62/234,125, filed 29 Sep. 2015 incorporated herein by reference.

FIELD OF THE INVENTION

The present invention relates to prolonging the hydrogenation activity of a process for the preparation of glycols from saccharide-containing feedstock.

BACKGROUND OF THE INVENTION

Glycols such as mono-ethylene glycol (MEG) and mono-propylene glycol (MPG) are valuable materials with a multitude of commercial applications, e.g. as heat transfer media, antifreeze, and precursors to polymers, such as PET. Ethylene and propylene glycols are typically made on an industrial scale by hydrolysis of the corresponding alkylene oxides, which are the oxidation products of ethylene and propylene, produced from fossil fuels.

In recent years, increased efforts have focussed on producing chemicals, including glycols, from non-petrochemical renewable feedstocks, such as sugar-based materials. The conversion of sugars to glycols can be seen as an efficient use of the starting materials with the oxygen atoms remaining intact in the desired product.

Current methods for the conversion of saccharides to glycols revolve around a two-step process of hydrogenolysis and hydrogenation, as described in Angew, Chem. Int. Ed. 2008, 47, 8510-8513.

Such two-step reaction requires at least two catalytic components. Patent application WO2015028398 describes a continuous process for the conversion of a saccharide-containing feedstock into glycols, in which substantially full conversion of the starting material and/or intermediates is achieved and in which the formation of by-products is reduced. In this process the saccharide-containing feedstock is contacted in a reactor vessel with a catalyst composition comprising at least two active catalytic components comprising, as a first active catalyst component with hydrogenation capabilities, one or more materials selected from+ transition metals from groups 8, 9 or 10 or compounds thereof, and, as a second active catalyst component with retro-aldol catalytic capabilities, one or more materials selected from tungsten, molybdenum and compounds and complexes thereof. Retro-aldol catalytic capabilities referred to herein means the ability of the second active catalyst component to break carbon-carbon bonds of sugars such as glucose to form retro-aldol fragments comprising molecules with carbonyl and hydroxyl groups. Glucose, which is an aldol product, for example, when broken into simple retro-aldol fragments yields glycolaldehyde.

It is well known in the art of chemicals manufacturing that catalysts may be described as homogeneous or heterogeneous, the former being those catalysts which exist and operate in the same phase as the reactants, while the latter are those that do not.

Typically, heterogeneous catalysts may be categorised into two broad groups. One group comprise the supported catalytic compositions where the catalytically active component is attached to a solid support, such as silica, alumina, zirconia, activated carbon or zeolites. Typically these are either mixed with the reactants of the process they catalyse, or they may be fixed or restrained within a reaction vessel and the reactants passed through it, or over it. The other group comprise catalytic compositions where the catalytically active component is unsupported, i.e. it is not attached, to a solid support, an example of this group is the Raney-metal group of catalysts. An example of a Raney-metal catalyst is Raney-nickel, which is a fine-grained solid, composed mostly of nickel derived from a nickel-aluminium alloy. The advantage of heterogeneous catalysts is that they can be retained in the reactor vessel during the process of extracting the unreacted reactants and the products from the reactor vessel, giving the operator the capability of using the same batch of catalysts many times over. However, the disadvantage of heterogeneous catalysts is that over time their activity declines, for reasons such as the loss or leaching of the catalytically active component from its support, or because the access of the reactants to the catalytically active component is hindered due to the irreversible deposition of insoluble debris on the catalyst's support. As their activity declines, catalysts need to be replaced, and for heterogeneous catalysts this inevitably requires the process that they catalyse to be stopped, and the reactor vessel to be opened up, to replace the deactivated catalyst with a fresh batch. Such down-time is costly to the operators of the process, as during such time no products can be produced, and such labour-intensive operations have cost implications.

A further complication of using heterogeneous catalysts is that the process of preparing the catalyst, and in particular the process of immobilising catalytically active components onto a solid support in a way that gives maximum catalytic activity can be difficult and time consuming.

Homogeneous catalysts are typically unsupported and operate in the same phase as the reactants of the reaction they catalyse. Therefore their preparation does not require any step(s) for immobilising the catalytically active components onto a solid support, and their addition to, and mixing with, the reactants of the reaction they catalyse is much easier. However, separation of the catalyst from the reactants becomes more difficult, and in some cases not possible. This means that, in general, homogeneous catalysts either require to be replenished more often than heterogeneous catalysts, and/or additional steps and hardware are required in the process to remove the catalyst from the reactants and reaction products, with an obvious impact on the overall economy of the processes that they catalyse.

Regarding the two-step continuous process of making glycols from saccharide-containing feedstock, as described in WO2015028398, the activities and robustness of the at least two catalytic components, each of which is typically a heterogeneous catalyst, can vary with respect to each other, and therefore if the activity of any one of them declines sooner than the activity of the other, the process of glycol production will not go to completion as efficiently as it was at the commencement of the process, forcing the operators to stop the process to recharge one or both of the catalysts. Alternatively, breakdown components of one of the two catalytic components may adversely affect the other's activity. Again in such a case, the operators of the process are forced to stop the process to recharge one or both of the catalysts. A particular problem is caused by the catalyst component with retro-aldol catalytic capabilities, as over time it degrades and components leach from it. In particular, insoluble tungsten and molybdenum compounds and complexes are formed from with the reactants in the reactor vessel over time. This problem is compounded by the deposition of organic degradation products, sintering of metal particles. Such insoluble matter attach to and clogs up the catalyst component with hydrogenation capability, especially if such catalyst component comprises porous solid support and/or is unsupported, but nevertheless has a porous surface topology (such as Raney-nickel). Further, the catalyst component with hydrogenation capability may also be poisoned by sulphur or other causes.

It would, therefore be, advantageous to be able to prepare an unsupported hydrogenation catalyst, which is suitable for the hydrogenation of retro-aldol fragments in the process for the preparation of glycols from saccharide-containing feedstock: (i) with minimal labour, including without the time consuming and tricky step of immobilisation of the catalytically active components on a solid support, (ii) which functions with the advantages of both a homogeneous-type and a heterogeneous-type catalysts, but without their respective disadvantages and (iii) which is unaffected by insoluble chemical species originating from the degradation of the catalyst component with retro-aldol catalytic capabilities, so that the two-step process of the conversion of saccharide-containing feedstock to glycols can be carried out in one reaction vessel, thus simplifying the process.

Further, in cases where the preparation of glycols from saccharide-containing feedstock is carried in a reactor vessel which was preloaded with a hydrogenation catalyst such as Raney-nickel (i.e. a hydrogenation catalyst other than the unsupported hydrogenation catalyst claimed herein) which is susceptible to the insoluble chemical species generated by the degradation of the catalyst component with retro-aldol catalytic capabilities, it would also be an advantage to be able to prolong reactor runtimes by, for example, being able to supplement the hydrogenation activity in the reactor vessel without stopping and opening up the reactor vessel, simply by, for example, the addition of the second hydrogenation catalyst via the liquid feed intake of the reactor vessel.

SUMMARY OF THE INVENTION

The present invention concerns a process for the preparation of glycols from a saccharide-containing feedstock comprising the steps of: (a) preparing a reaction mixture in a reactor vessel comprising the saccharide-containing feedstock, a solvent, a catalyst component with retro-aldol catalytic capabilities and a first hydrogenation catalyst comprising an element selected from groups 8, 9 and 10 of the periodic table; (b) supplying hydrogen gas to the reaction mixture in the reactor vessel; (c) monitoring the activity of the first hydrogenation catalyst; (d) preparing a second hydrogenation catalyst by contacting in a reactor a catalyst precursor comprising one or more elements selected from chromium and groups 8, 9, 10 and 11 of the periodic table with hydrazine to convert the catalyst precursor into the second hydrogenation catalyst; and (e) when the hydrogenation activity declines, supplying the second hydrogenation catalyst to the reactor vessel to supplement the declined hydrogenation activity in the reactor vessel.

The hydrogenation step in the process for the production of glycols from a saccharide-containing feedstock as described in WO2015028398 may be carried out with a Raney-metal type catalyst, which is readily available and is relatively cheap. Said hydrogenation step can also be carried out with other supported hydrogenation catalysts comprising an element selected from groups 8, 9 and 10 of the periodic table (i.e. other than the second hydrogenation catalyst claimed herein). However, because the process described in WO2015028398 is carried out in a single reactor vessel in the presence of a catalyst component with retro-aldol catalytic capabilities, both the Raney-metal hydrogenation catalyst and the other supported hydrogenation catalysts comprising an element selected from groups 8, 9 and 10 of the periodic table are prone to deactivation by the degradation products of the catalyst component with retro-aldol catalytic capabilities.

The inventors of the present processes have surprisingly found that a second hydrogenation catalyst for the production of glycols from a saccharide-containing feedstock, which can be prepared with minimal labour, is resistant to deactivation by the degradation products of the catalyst component with retro-aldol catalytic capabilities, and can be supplied to the reactor vessel without stopping the process to supplement the declining activity of the Raney-metal hydrogenation catalyst and the other supported hydrogenation catalysts.

DETAILED DESCRIPTION OF THE INVENTION

Figure 1:
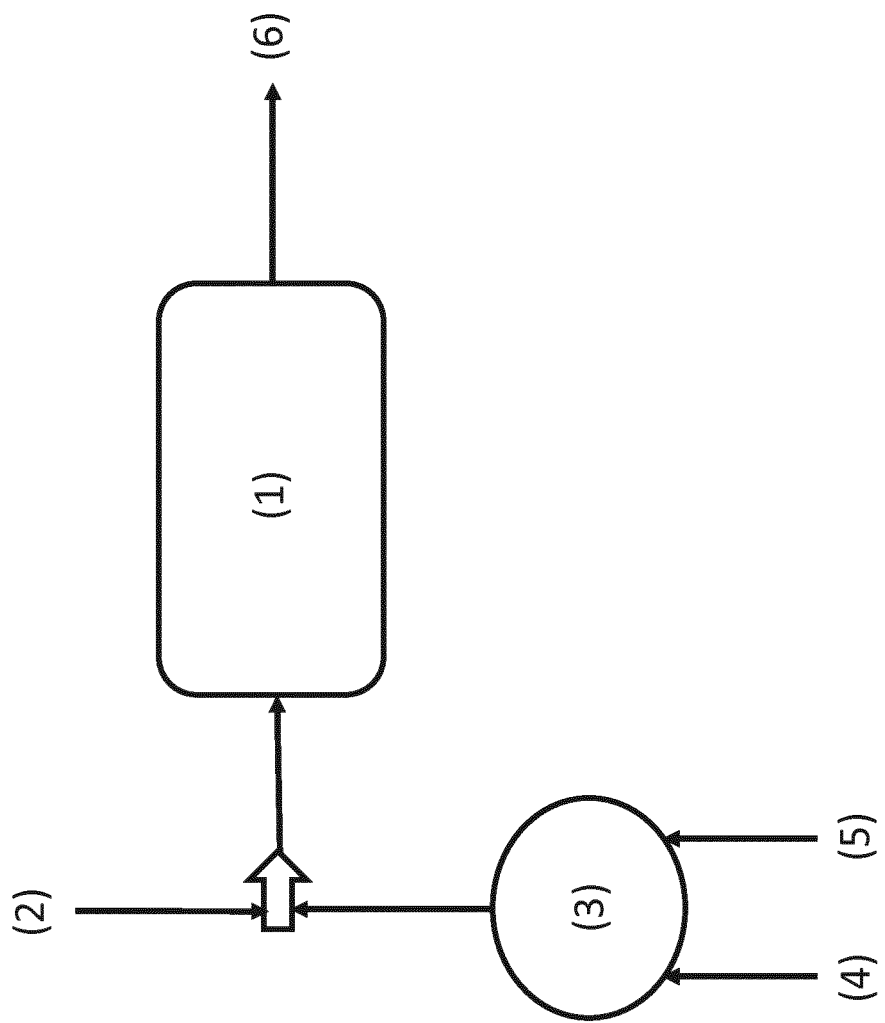
FIG. 1 shows a simplified schematic diagram of the embodiment where a single reactor vessel is used for the process for the preparation of glycols from a saccharide-containing feedstock.

In the present invention, a reaction mixture comprising a saccharide-containing feedstock, a solvent, a catalyst component with retro-aldol catalytic capabilities and a first hydrogenation catalyst is prepared in a reactor vessel, and hydrogen gas is supplied to the reaction mixture in the reactor vessel while the reactor vessel is maintained at a temperature and a pressure. Under these conditions, the catalyst component with retro-aldol catalytic capabilities converts the sugars in the saccharide-containing feedstock into retro-aldol fragments comprising molecules with carbonyl and hydroxyl groups, and in the presence of hydrogen, the first hydrogenation catalyst converts the these retro-aldol fragments into glycols.

The glycols produced by the process of the present invention are preferably 1,2-butanediol, MEG and MPG, and more preferably MEG and MPG, and most preferably MEG. The mass ratio of MEG to MPG glycols produced by the process of the present invention is preferably 5:1, more preferably 7:1 at 230° C. and 8 MPa.

The saccharide-containing feedstock for the process of the present invention comprises starch. It may also comprise one or further saccharides selected from the group consisting of monosaccharides, disaccharides, oligosaccharides and polysaccharides. Examples of suitable disaccharides include glucose, sucrose and mixtures thereof. Examples of suitable oligosaccharides and polysaccharides include cellulose, hemicelluloses, glycogen, chitin and mixtures thereof.

In one embodiment, the saccharide-containing feedstock for said processes is derived from corn.

Alternatively, the saccharide-containing feedstock may be derived from grains such as wheat or, barley, from rice and/or from root vegetables such as potatoes, cassava or sugar beet, or any combinations thereof. In another embodiment, a second generation biomass feed such as lignocellulosic biomass, for example corn stover, straw, sugar cane bagasse or energy crops like Miscanthus or sweet sorghum and wood chips, can be used as, or can be part of, the saccharide-containing feedstock.

A pre-treatment step may be applied to remove particulates and other unwanted insoluble matter, or to render the carbohydrates accessible for hydrolysis and/or other intended conversions.

If required, further pre-treatment methods may be applied in order to produce the saccharide-containing feedstock suitable for use in the present invention. One or more such methods may be selected from the group including, but not limited to, sizing, drying, milling, hot water treatment, steam treatment, hydrolysis, pyrolysis, thermal treatment, chemical treatment, biological treatment, saccharification, fermentation and solids removal.

After the pre-treatment, the treated feedstock stream is suitably converted into a solution, a suspension or a slurry in a solvent.

The solvent may be water, or a $C_1$ to $C_6$ alcohol or polyalcohol, or mixtures thereof. Suitably C1 to C6 alcohols include methanol, ethanol, 1-propanol and isopropanol. Suitably polyalcohols include glycols, particularly products of the hydrogenation reaction, glycerol, erythritol, threitol, sorbitol, 1,2-hexanediol and mixtures thereof. More suitably, the poly alcohol may be glycerol or 1,2-hexanediol. Preferably, the solvent is water. Further solvent may also be added to a reactor vessel or reactor vessels in a separate feed stream or may be added to the treated feedstock stream before it enters the reactor. Said solvent may be water, or a $C_1$ to $C_6$ alcohol or polyalcohol, or mixtures thereof. Suitably C1 to C6 alcohols include methanol, ethanol, 1-propanol and isopropanol. Suitably polyalcohols include glycols, particularly products of the hydrogenation reaction, glycerol, erythritol, threitol, sorbitol, 1,2-hexanediol and mixtures thereof. More suitably, the poly alcohol may be glycerol or 1,2-hexanediol. Preferably, both solvents are the same. More preferably, both solvents comprise water. Most preferably, both solvents are water.

The concentration of the saccharide-containing feedstock as a solution in the solvent supplied to the reactor vessel is at most at 80% wt., more preferably at most at 60% wt. and more preferably at most at 45% wt. The concentration of the saccharide-containing feedstock as a solution in the solvent supplied to the reactor vessel is at least 5% wt., preferably at least 20% wt. and more preferably at least 35% wt.

Preferably, the active catalytic components of the catalyst component with retro-aldol catalytic capabilities comprises of one or more compound, complex or elemental material comprising tungsten, molybdenum, vanadium, niobium, chromium, titanium or zirconium. More preferably the active catalytic components of the catalyst component with retro-aldol catalytic capabilities comprises of one or more material selected from the list consisting of tungstic acid, molybdic acid, ammonium tungstate, ammonium metatungstate, sodium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulphate, titanium ethoxide, zirconium acetate, zirconium carbonate, zirconium hydroxide, niobium oxides, niobium ethoxide, and combinations thereof. The metal component is in a form other than a carbide, nitride, or phosphide. Preferably, the second active catalyst component comprises one or more compound, complex or elemental material selected from those containing tungsten or molybdenum.

In one embodiment, the active catalytic components of the catalyst component with retro-aldol catalytic capabilities are supported on a solid support, and operates as a heterogeneous catalyst. The solid supports may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

In another embodiment, the catalyst component with retro-aldol catalytic capabilities is unsupported, and operates as a homogeneous catalyst. Preferably, in this embodiment the active catalytic components of the catalyst component with retro-aldol catalytic capabilities is metatungstate, which is delivered into the reactor vessel as an aqueous solution of sodium metatungstate.

The weight ratio of the catalyst component with retro-aldol catalytic capabilities (based on the amount of metal in said composition) to the saccharide-containing feedstock is suitably in the range of from 1:100 to 1:1000.

Suitable reactor vessels that can be used in the process of the preparation of glycols from a saccharide-containing feedstock include continuous stirred tank reactors (CSTR), plug-flow reactors, slurry reactors, ebullated bed reactors, jet flow reactors, mechanically agitated reactors, bubble columns, such as slurry bubble columns and external recycle loop reactors. The use of these reactor vessels allows dilution of the reaction mixture to an extent that provides high degrees of selectivity to the desired glycol product (mainly ethylene and propylene glycols). In one embodiment, there is a single reactor vessel, which is preferably a CSTR.

There may be more than one reactor vessel used to carry out the process of the present invention. The more than one reactor vessels may be arranged in series, or may be arranged in parallel with respect to each other. In a further embodiment, two reactor vessels arranged in series, preferably the first reactor vessel is a CSTR, the output of which is supplied to a second reactor vessel, which is a plug-flow reactor. The advantage provided by such two reactor vessel embodiment is that the retro-aldol fragments produced in the CSTR have a further opportunity to undergo hydrogenation in the second reactor, thereby increasing the glycol yield of the process.

Preferably, the process of the present reaction takes place in the absence of air or oxygen. In order to achieve this, it is preferable that the atmosphere in the reactor vessel be evacuated and replaced with hydrogen repeatedly, after loading of any initial reactor vessel contents, before the reaction starts.

The process of the present invention takes place in the presence of hydrogen. Hydrogen is supplied into the reactor vessel under pressure in a manner common in the art. Hydrogen is supplied into both the reactor vessels under pressure.

The reaction mixture comprises a first hydrogenation catalyst. The first hydrogenation catalyst comprises an element selected from groups 8, 9 and 10 of the periodic table. In one embodiment, the first hydrogenation catalyst is a Raney-metal type catalyst, preferably a Raney-nickel catalyst. In another embodiment, the first hydrogenation catalyst is a supported hydrogenation catalyst, such as ruthenium supported on activated carbon. Suitable supports of the supported hydrogenation catalyst are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

In the embodiment where there is a single reactor vessel used for the process for the preparation of glycols from a saccharide-containing feedstock, the reaction temperature in the reactor vessel is suitably at least 130° C., preferably at least 150° C., more preferably at least 170° C., most preferably at least 190° C. In such embodiment, the temperature in the reactor vessel is suitably at most 300° C., preferably at most 280° C., more preferably at most 270° C., even more preferably at most 250° C. Preferably, the reactor vessel is heated to a temperature within these limits before addition of any reaction mixture and is controlled at such a temperature to facilitate the completion of the reaction.

In the embodiment with a CSTR followed by a plug-flow reactor arranged in series, the reaction temperature in the CSTR is suitably at least 130° C., preferably at least 150° C., more preferably at least 170° C., most preferably at least 190° C. The temperature in the reactor vessel is suitably at most 300° C., preferably at most 280° C., more preferably at most 250° C., even more preferably at most 230° C. In the embodiment with a CSTR followed by a plug-flow reactor arranged in series, the reaction temperature in the plug-flow reactor is suitably at least 50° C., preferably at least 60° C., more preferably at least 80° C., most preferably at least 90° C. The temperature in such reactor vessel is suitably at most 250° C., preferably at most 180° C., more preferably at most 150° C., even more preferably at most 120° C. Preferably, each reactor vessel is heated to a temperature within these limits before addition of any reaction mixture and is controlled at such a temperature to facilitate the completion of the reaction.

In the embodiment where there is a single reactor vessel used for the process for the preparation of glycols from a saccharide-containing feedstock, the pressure in the reactor vessel in which the reaction mixture is contacted with hydrogen in the presence of the catalyst composition described herein is suitably at least 3 MPa, preferably at least 5 MPa, more preferably at least 7 MPa. In such embodiment, the pressure in the reactor vessel is suitably at most 12 MPa, preferably at most 10 MPa, more preferably at most 8 MPa. Preferably, the reactor vessel is pressurised to a pressure within these limits by addition of hydrogen before addition of any reaction mixture and is controlled at such a pressure to facilitate the completion of reaction through on-going addition of hydrogen.

In the embodiment where there are two reactor vessels arranged in series, the pressure in each reactor vessel is suitably at least 3 MPa, preferably at least 5 MPa, more preferably at least 7 MPa. In such embodiment, the pressure in each reactor vessel is suitably at most 12 MPa, preferably at most 10 MPa, more preferably at most 8 MPa. Preferably, each reactor vessel is pressurised to a pressure within these limits by addition of hydrogen before addition of any reaction mixture and is controlled at such a pressure to facilitate the completion of reaction through on-going addition of hydrogen.

In the embodiment where there is a single reactor vessel used for the process for the preparation of glycols from a saccharide-containing feedstock, the residence time in the reactor vessel of the reaction mixture is suitably at least 1 minute, preferably at least 2 minutes, more preferably at least 5 minutes, and suitably the residence time in the reactor vessel is no more than 5 hours, preferably no more than 2 hours, more preferably no more than 1 hour. In the embodiment where there are two reactor vessels arranged in series, the residence time for each of the vessels is suitably at least 1 minute, preferably at least 2 minutes, more preferably at least 5 minutes, and is no more than 5 hours, preferably no more than 2 hours, more preferably no more than 1 hour.

The second hydrogenation catalyst is prepared in a reactor by contacting a catalyst precursor with hydrazine.

The catalyst precursor is a metal salt or a metal complex. In one embodiment, the catalyst precursor comprises a cation of an element selected from chromium and groups 8, 9, 10 and 11 of the periodic table. Preferably, the cation is selected from the group consisting of chromium, iron, ruthenium, cobalt, rhodium, iridium, nickel, palladium, platinum and copper. More preferably the cation of the salt is selected from the group comprising nickel, cobalt and ruthenium. Most preferably, the catalyst precursor comprises a ruthenium cation. In another embodiment, the catalyst precursor comprises a mixture of cations of more than one element selected from chromium and groups 8, 9, 10 and 11 of the periodic table. Preferably, the cations are selected from the group of elements consisting of chromium, iron, ruthenium, cobalt, rhodium, iridium, nickel, palladium, platinum and copper. Suitable examples of such mixture of cations may be a combination of nickel with palladium, or a combination of palladium with platinum, or a combination of nickel with ruthenium, or a combination of chromium with copper. The catalyst precursor is a metal salt or a metal complex. In one embodiment, the catalyst precursor comprises an anion selected from the group consisting of anions of organic carboxylic acids and any inorganic anion. In the case of both the organic and the inorganic anions, the anion must form a salt or a complex with the cations listed above, which is soluble in a mixture comprising the saccharide-containing feedstock, the solvent and the glycols. Preferably, the anion is selected from formate, acetate, oxalate, propionate, lactate, glycolate, stearate, acetylacetonate, nitrate, chloride, bromide, iodide and sulphate. More preferably, the anion is selected from formate, acetate, acetylacetonate and nitrate. Even more preferably, the anion is selected from formate, acetate and acetylacetonate, and most preferably, the anion is formate or acetate. In the embodiment where the catalyst precursor comprises more than one cation, the anion of each of the metal salts or metal complexes may be any one of the anions listed above, with the proviso that each metal salt or each metal complex must be soluble in a mixture comprising the saccharide-containing feedstock, the solvent and the glycols.

In the process of the present invention for the preparation of a second hydrogenation catalyst, a solution of hydrazine is prepared. Preferably the concentration of the hydrazine in such solution is at the most 1000 mM, more preferably at the most 500 mM, and most preferably 125 mM. Preferably the concentration of the hydrazine in such solution is at least 10 mM, more preferably at least 50 mM, and most preferably at least 75 mM.

In the process of the present invention for the preparation of a second hydrogenation catalyst, a solution of the catalyst precursor is prepared. Preferably, based on the concentration of the cation, the concentration of the catalyst precursor in such solution is at the most 1000 mM, more preferably at the most 500 mM, and most preferably 125 mM. Preferably, based on the concentration of the cation, the concentration of the catalyst precursor in such solution is at least 10 mM, more preferably at least 50 mM, and most preferably at least 75 mM.

The solution of hydrazine comprises a solvent. Preferably, such solvent is water and/or a solution of glycols in water, and/or the product stream from the reactor vessel used for the process of producing glycols described herein.

The solution of the catalyst precursor comprises a solvent. Preferably, such solvent is water and/or a solution of glycols in water and/or the product stream from the reactor vessel used for the process of producing glycols described herein.

Preferably, the choice of reactors that can be used to carry out such hydrazine treatment of the catalyst precursor are batch reactors, continuous stirred tank reactors (CSTR), pipeline reactors, or a combination comprising a CSTR followed by a pipeline reactor. More preferably, the choice of reactor is a CSTR followed by a pipeline reactor, and most preferably the choice of reactor is a pipeline reactor.

The solution of the catalyst precursor and the solution of hydrazine are pumped into the reactor, and mixed together in the reactor. The ratio of the catalyst precursor to hydrazine pumped into the reactor, on a stoichiometry basis, is preferably at most a ratio of 1.10:1, more preferably at most a ratio of 1.05:1 and most preferably at most a ratio of 1.02:1. The ratio of the solution of the catalyst precursor to the solution of hydrazine pumped into the reactor is preferably at least a ratio of 0.90:1, more preferably at least a ratio of 0.95:1 and most preferably at least a ratio of 0.98:1. The stoichiometric basis of the reduction by hydrazine is 0.5 mole of hydrazine per mole of (2+) charged cation. In the embodiment where the cation is Ru(3+), the stoichiometric equivalence of hydrazine required to reduce this cation to Ru metal is 0.75 moles of hydrazine per mole of Ru(3+). In the embodiment where the catalyst precursor comprises more than one cation, the ratio of the catalyst precursor to hydrazine pumped into the reactor is calculated on a stoichiometry basis for each cation.

The ratio of the catalyst precursor to hydrazine is important in that, minimal unreacted hydrazine must remain following the hydrazine treatment of the catalyst precursor. As the product of this reaction is supplied directly into the reactor vessel for the preparation of glycols from saccharide-containing feedstock, any unreacted hydrazine that enters the glycol preparation reaction will react with the saccharide-containing feedstock and form hydrazones, which are molecules that do not contribute to the production of glycols. Conversely, insufficient hydrazine will fail to convert the entire catalyst precursor into the second hydrogenation catalyst.

The solution of the catalyst precursor and the solution of hydrazine are preferably maintained in the reactor at a temperature of at least 20° C., more preferably at a temperature of at least 25° C. and most preferably at a temperature of at least 30° C. The solution of the catalyst precursor and the solution of hydrazine are preferably maintained in the reactor at a temperature of at most 230° C., more preferably at a temperature of at most 100° C. and most preferably at a temperature of at most 50° C.

The residence time of the mixture of the solution of the catalyst precursor and the solution of hydrazine in the reactor is preferably at most 60 min, more preferably at most 30 min and most preferably at most 5 min. The residence time of the mixture of the solution of the catalyst precursor and the solution of hydrazine in the reactor is preferably at least 0.1 min, more preferably at least 0.5 min and most preferably at least 1 min.

The output stream obtained from the reactor for contacting the solution of the catalyst precursor with the solution of hydrazine comprises nitrogen gas and the second hydrogenation catalyst. The nitrogen gas is released from this output stream and the remainder of the output stream is pumped into the reactor vessel for the conversion of saccharide-containing feedstock to glycols. Other than the release of the nitrogen gas, no further treatment of the output stream is necessary, however, during the hydrazine treatment the output stream becomes acidic, and if needed, it can be neutralised by any techniques known to the skilled person, such as the addition of sodium hydroxide, or sodium carbonate, either during the mixing of the solution of hydrazine with the solution of catalyst precursor, or at a later stage on the output stream itself.

The activity of the first hydrogenation catalyst can be monitored in a number of ways by measuring certain indications. For example, decline in product yield (e.g. MEG levels), decline in the formation of sugar alcohols like glycerin, erythritol, threitol and sorbitol, decline in pH due to formation of increased amounts of organic acids, increase in the levels of hydroxyketones, 2,3-butanediol and 2,3-pentanediol, increase in the levels of C3, C4 and C6 components relative to C2, are all indications of a decline in hydrogenation activity. One or more of these indications may be monitored at any one time. In one embodiment, the pH of the glycol product stream is monitored and the pH value of 4 is defined as a threshold. As the glycol production process described herein proceeds, the glycol product stream becomes increasingly acidic, and a pH value of 4 or lower is an indication that the hydrogenation catalytic activity has declined. Each time the level of pH is at or below this threshold level, a quantity of second hydrogenation catalyst may be supplied into the reactor vessel to supplement the hydrogenation activity in the reactor vessel(s).

The weight ratio of the second hydrogenation catalyst (based on the amount of metal in said composition) to the saccharide-containing feedstock is suitably in the range of from 1:100 to 1:1000.

The inventors believe that the second hydrogenation catalyst comprises catalytically active micron-sized metal particles. They further believe that the surface topology of the catalytically active micron-sized particles is smooth and does not contain any significant pores inside the particles, making the second hydrogenation catalyst resistant to the attachment of insoluble chemical species originating from the catalyst component with retro-aldol catalytic capabilities during the process for the preparation of glycols from a saccharide-containing feedstock.

The process of the application therefore provides the following three solutions for the producers of glycols from saccharide-containing feedstock.

Firstly, the process of preparing the second hydrogenation catalyst by contacting the catalyst precursor with hydrazine treatment is a quick and easy, and its output stream does not contain appreciable amount of hydrazine or any other chemical species that might adversely affect the glycol production from the saccharide-containing feedstock. This means that such stream can be directly mixed with the saccharide-containing feedstock, and no hydrazones are produced during the glycol production process in the reactor vessel(s), and thus the glycol yield is not compromised.

Secondly, the most preferable embodiment of the catalyst precursor comprises a ruthenium cation. Ruthenium and other rare transition metals are expensive commodities. The processes of the present invention allows the process for the production of glycols from saccharide-containing feedstock to begin with a cheaper catalyst, even though its activity will decline due to deactivation by the insoluble chemical species generated by the degradation of the catalyst component with retro-aldol catalytic capabilities.

Thirdly, it is important to the operators of the process for the production of glycols from saccharide-containing feedstock to run the process without interruption for periods up to 8,000 hours. The second hydrogenation catalyst, which can be supplied to the reactor vessel as if it is a homogeneous catalyst, therefore provides the means by which the decline in hydrogenation catalytic activity due to insoluble chemical species generated by the degradation of the catalyst component with retro-aldol catalytic capabilities can be overcome.

DETAILED DESCRIPTION OF THE DRAWINGS

FIG. 1 shows a simplified schematic diagram of the embodiment where a single reactor vessel (1) used for the process for the preparation of glycols from a saccharide-containing feedstock. A reaction mixture (2) comprising the saccharide-containing feedstock, a solvent, a catalyst component with retro-aldol catalytic capabilities and a first hydrogenation catalyst comprising an element selected from groups 8, 9 and 10 of the periodic is supplied to reactor vessel (1) together with the outflow from reactor (3). The reactor (3) is used to prepare the second hydrogenation catalyst by contacting a catalyst precursor (4) with hydrazine (5). The outflow from the reactor (3) comprises the second hydrogenation catalyst. The process for the preparation of glycols from a saccharide-containing feedstock comprises the actions of a retro-aldol catalysis and a first hydrogenation catalysis. The first hydrogenation catalyst is adversely affected by the degradation products of the catalyst component with retro-aldol catalytic capabilities, so its activity is monitored, and when its activity falls, as defined by a threshold, further outflow from a reactor (3) may be supplied to reactor vessel (1) to supplement the hydrogenation activity in reactor vessel (1). The product of the process comprising glycols (6) is obtained as the outflow from reactor vessel (1).

Figure 2:
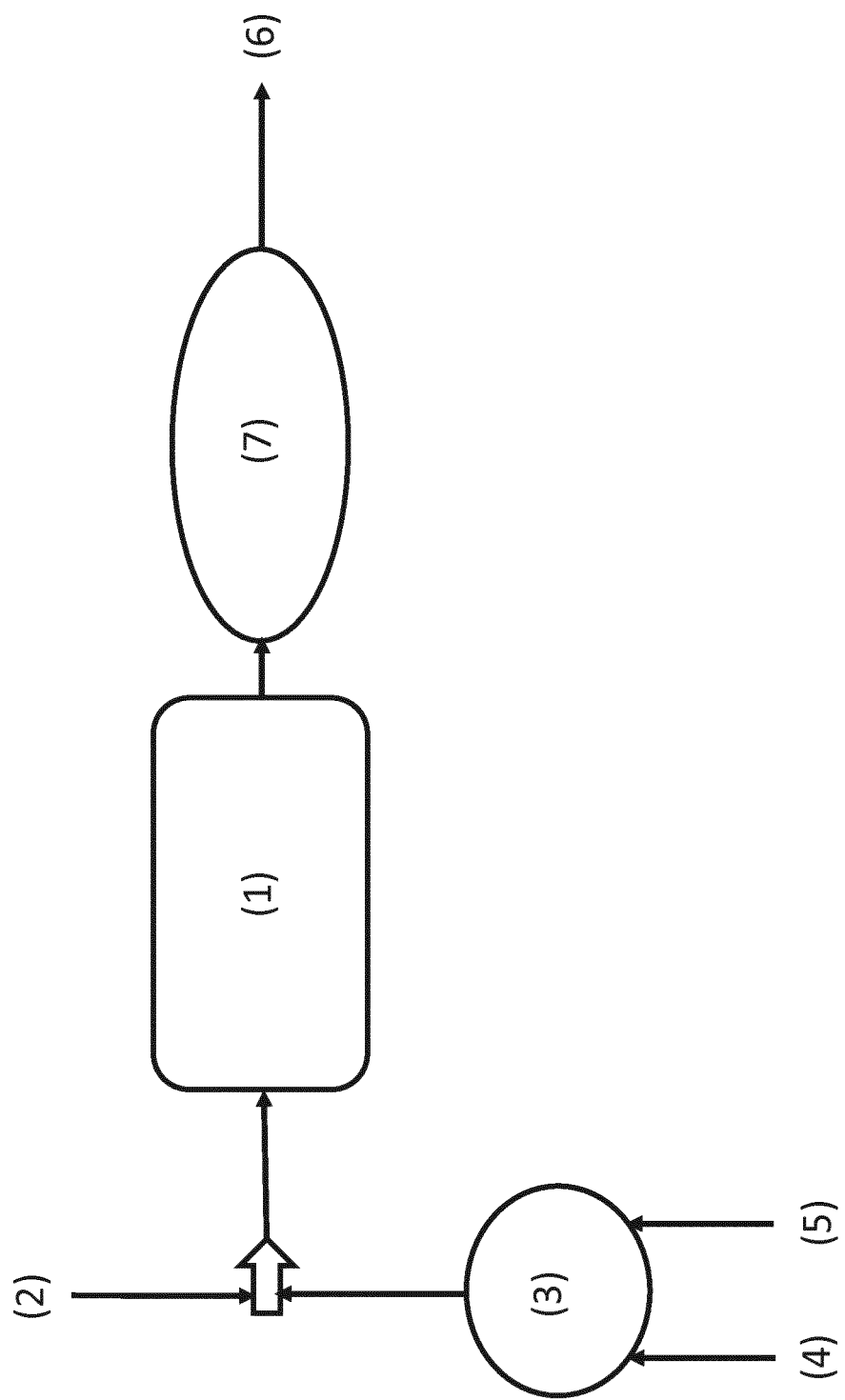
FIG. 2 shows a simplified schematic diagram of the embodiment where two reactor vessels are arranged in series are used for the process for the preparation of glycols from a saccharide-containing feedstock.

FIG. 2 shows a simplified schematic diagram of the embodiment where two reactor vessels, (1) and (7), are arranged in series. Reactor vessel (1) is a continuous stirred tank reactors and reactor vessel (7) is a plug-flow reactor. The outflow from reactor vessel (1) is supplied to reactor vessel (7) to increase the glycol product levels. Other features of this embodiment, and their respective numbering, are the same as the embodiment described in FIG. 1.

That which is claimed is:

1. A process for the preparation of glycols from a saccharide-containing feedstock comprising the steps of:

(a) preparing a reaction mixture in a reactor vessel comprising the saccharide-containing feedstock, a solvent, a catalyst component with retro-aldol catalytic capabilities comprising one or more compound, complex or elemental material selected from the group comprising tungsten, molybdenum, vanadium, niobium, chromium, titanium and zirconium and a first hydrogenation catalyst comprising an element selected from groups 8, 9 and 10 of the periodic table;
   (b) supplying hydrogen gas to the reaction mixture in the reactor vessel;
   (c) monitoring the hydrogenation activity in the reactor vessel;
   (d) preparing a second hydrogenation catalyst by contacting in a reactor a catalyst precursor comprising a metal salt or a metal complex of one or more elements selected from chromium and groups 8, 9, 10 and 11 of the periodic table with hydrazine to convert the catalyst precursor into the second hydrogenation catalyst; and
   (e) when the hydrogenation activity declines, supplying the second hydrogenation catalyst to the reactor vessel to supplement the declined hydrogenation activity in the reactor vessel.

2. The process according to claim 1, wherein the glycols comprise ethylene glycol and 1, 2-propylene glycol.

3. The process according to claim 1, wherein the saccharide-containing feedstock comprises one or more saccharide selected from a group consisting of monosaccharides, disaccharides, oligosaccharides and polysaccharides.

4. The process according to claim 1, wherein the solvent is water, or a C1, C2, C3, C4, C5 or a C6 alcohol or polyalcohol, or any combination of mixtures thereof.

5. The process according to claim 1, wherein the catalyst component with retro-aldol catalytic capabilities comprises tungsten.

6. The process according to claim 1, wherein the first hydrogenation catalyst is Raney-nickel.

7. The process according to claim 1, wherein the catalyst precursor comprises one or more cations of chromium, iron, ruthenium, cobalt, rhodium, iridium, nickel, copper, palladium and platinum.

8. The process according to claim 1, wherein the catalyst precursor comprises ruthenium cations.

9. The process according to claim 1, wherein the catalyst precursor comprises an anion selected from a group consisting of carboxylates, acetylacetonate and inorganic anions, which in all cases forms a salt or a complex that is soluble in a solvent mixture comprising the saccharide-containing feedstock, the solvent and the glycols.

10. The process according to claim 1, wherein the precursor comprises formate or acetate.

* * * * *